US009717751B2

(12) United States Patent
Auclair et al.

(10) Patent No.: US 9,717,751 B2
(45) Date of Patent: Aug. 1, 2017

(54) CHITIN OR DERIVATIVES THEREOF FOR THE PREVENTION AND/OR TREATMENT OF PARASITOSES

(71) Applicant: LESAFFRE ET COMPAGNIE, Paris (FR)

(72) Inventors: Eric Auclair, Aveline (FR); Jean-Philippe Marden, Labege (FR); Fabrice Laurent, Rochecorbon (FR); Sonia Lacroix-Lamande, Bueil en Tourain (FR)

(73) Assignee: LESAFFRE ET COMPAGNIE, Paris (FR)

( * ) Notice: Subject to any disclaimer, the term of this patent is extended or adjusted under 35 U.S.C. 154(b) by 0 days.

(21) Appl. No.: 14/648,919

(22) PCT Filed: Dec. 10, 2013

(86) PCT No.: PCT/FR2013/053010
§ 371 (c)(1),
(2) Date: Jun. 2, 2015

(87) PCT Pub. No.: WO2014/091138
PCT Pub. Date: Jun. 19, 2014

(65) Prior Publication Data
US 2015/0297632 A1    Oct. 22, 2015

(30) Foreign Application Priority Data

Dec. 14, 2012  (FR) ...................... 12 62072

(51) Int. Cl.
| A61K 36/00 | (2006.01) |
| A61K 31/722 | (2006.01) |
| A61K 45/06 | (2006.01) |
| A61K 31/7008 | (2006.01) |
| A61K 33/04 | (2006.01) |
| A61K 33/44 | (2006.01) |
| A61K 36/8962 | (2006.01) |
| A61K 36/899 | (2006.01) |
| A61K 35/742 | (2015.01) |
| A61K 35/747 | (2015.01) |
| A61K 36/064 | (2006.01) |
| A61K 36/53 | (2006.01) |
| A61K 36/54 | (2006.01) |

(52) U.S. Cl.
CPC ........ *A61K 31/722* (2013.01); *A61K 31/7008* (2013.01); *A61K 33/04* (2013.01); *A61K 33/44* (2013.01); *A61K 35/742* (2013.01); *A61K 35/747* (2013.01); *A61K 36/064* (2013.01); *A61K 36/53* (2013.01); *A61K 36/54* (2013.01); *A61K 36/899* (2013.01); *A61K 36/8962* (2013.01); *A61K 45/06* (2013.01)

(58) Field of Classification Search
None
See application file for complete search history.

(56) References Cited

U.S. PATENT DOCUMENTS

2003/0185904 A1   10/2003   Reynolds
2012/0201916 A1    8/2012   Miller

FOREIGN PATENT DOCUMENTS

| CN | 1692782 A | * | 11/2005 |
| JP | 2001-081007 | | 3/2001 |
| JP | 2010265194 A | * | 11/2010 |
| KR | 185267 B1 | * | 5/1999 |
| KR | 100 799 652 | | 1/2008 |
| WO | 03/057233 | | 7/2003 |

OTHER PUBLICATIONS

Chafer, Fungal decay and shelf life of oranges coated with chitosan and bergamot, thyme, and tea tree essential oils. Journal of food science, (Aug. 2012) vol. 77, No. 8, pp. E182-E187.*
Kokalis-Burelle, Chitin amendments for suppression of plant parasitic nematodes and fungal pathogens. Phytopathology, (Jun. 2001) vol. 91, No. 6 Supplement, pp. S168.*
Luzardo Alvarez, In vitro evaluation of the suppressive effect of chitosan/poly(vinyl alcohol) microspheres on attachment of C. parvum to enterocytic cells. European journal of pharmaceutical sciences: official journal of the European Federation for Pharmaceutical Sciences, (Aug. 30, 2012) vol. 47, No. 1, pp. 215-227).*
Radwan et al, Integrated management of Meloidogyne incognita infecting tomato using bio-agents mixed with either oxamyl or organic amendments. Nematologia Mediterranea (2011), vol. 39, No. 2, pp. 151-156.*
El-Ezz et al, Therapeutic effect of onion (*Allium cepa*) and cinnamon (*Cinnamomum zeylanicum*) oils on cryptosporidiosis in experimentally infected mice. Global Veterinaria (2011), vol. 7, No. 2, pp. 179-183.*
Zuckerman et al, Chitin, a structural component of Cryptosporidium oocyst walls. Journal of Eukaryotic Microbiology, (Mar.-Apr. 2000. vol. 47, No. 2, pp. 13A.*
International Search Report dated Feb. 19, 2014, which issued during prosecution of International Application No. PCT/FR2013/053010.
International Preliminary Report on Patentability and Written Opinion dated Jun. 16, 2015, which issued during prosecution of International Application No. PCT/FR2013/053010.
V. Giatrakou, et al. "Combined Chitosan-Thyme Treatments with Modified Atmosphere Packaging on a Ready-to-Cook Poultry Product" Journal of Food Protection 73(4):663-669, Apr. 2010.

(Continued)

*Primary Examiner* — Qiuwen Mi
(74) *Attorney, Agent, or Firm* — Vedder Price P.C.; Thomas J. Kowalski; Deborah L. Lu

(57) ABSTRACT

The subject matter of the present invention is the use of chitin or a derivative of chitin for preventing and/or treating parasitoses, and in particular cryptosporidiosis. The present invention also pertains to a composition that comprises at least one base agent chosen from among chitin or a derivative of chitin and at least one secondary agent chosen from among an agent for stimulating immunity and an antiparasite agent, as well as the use of same for preventing and/or treating parasitoses, in particular cryptosporidiosis.

5 Claims, 1 Drawing Sheet

(56) References Cited

OTHER PUBLICATIONS

Claudia Juliano, et al "In vitro study on the anticandidal activity of *Melaleuca alternifolia* (tea tree) essential oil combined with chitosan" Flavour and Fragrance Journal 23(4):227-231, Jul. 2008.
S. Petrou, et al. "Chitosan dipping or oregano oil treatments, singly or combined on modified atmosphere packaged chicken breast meat" International Journal of Food Microbiology 156(3):264-271, Apr. 2012.
Y. Pranoto, et al. "Enhancing antimicrobial activity of chitosan films by incorporating garlic oil, potassium sorbate and nisin" LWT—Food Science and Technology, 38(8):859-865, Dec. 2005.

\* cited by examiner

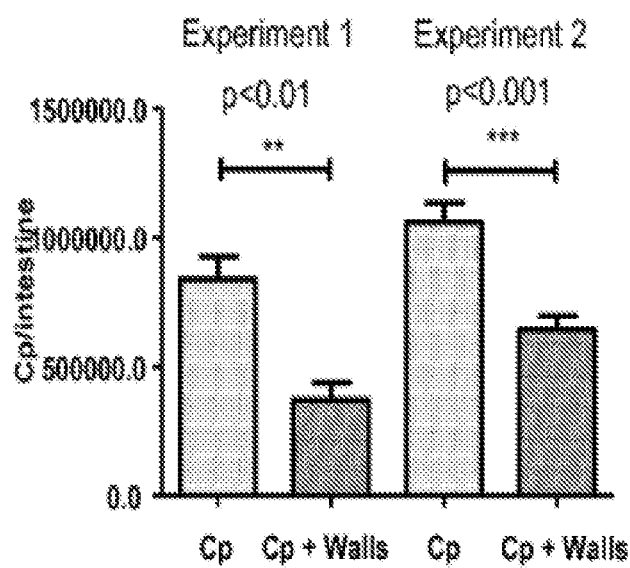

CHITIN OR DERIVATIVES THEREOF FOR THE PREVENTION AND/OR TREATMENT OF PARASITOSES

RELATED PATENT APPLICATIONS

The present application is filed pursuant to 35 U.S.C. 371 as a U.S. National Phase Application of International Patent Application No. PCT/FR2013/053010, which was filed on Dec. 10, 2013, which published as WO 2014/091138 on Jun. 19, 2014 and claims the benefit of priority to French Patent Application No. FR 1262072 filed on Dec. 14, 2012. The content of each of the aforementioned Patent Applications is incorporated herein by reference in its entirety.

TECHNICAL FIELD

The present invention relates to the field of the prevention and/or treatment of parasitoses, in particular cryptosporidiosis, in humans and animals.

TECHNICAL BACKGROUND

Cryptosporidiosis is a disease associated with a protozoan, *Cryptosporidium*, which has very significant negative economic consequences in livestock, because of the increase in mortality and the delays in growth, the cost of the veterinary care and the treatments that it creates, and also the increase in working time for managing the sick animals.

Cryptosporidiosis also affects humans and can have dramatic consequences in immunodepressed patients, in particular in patients suffering from HIV, and also newborns.

The principal clinical sign associated with cryptosporidiosis is acute diarrhea. The other clinical signs associated with diarrhea are in particular dehydration, intense weakness, a loss of appetite and colic. These various clinical signs can lead to death, in particular of young animals.

Halofuginone is the only medicament which has a marketing authorization in France for the prevention and/or treatment of cryptosporidiosis in calves.

However, not only is the efficacy of halofuginone partial, but it exhibits a certain toxicity, and a risk of cryptosporidia developing resistance to this compound has been reported (see Silverlas et al., Preventive Veterinary Medicine, 2009, 91: 73-84).

Moreover, no medicament is registered for the treatment of cryptosporidiosis in kids and lambs.

In humans, nitazoxanide and paromomycin have been used in the treatment of cryptosporidiosis. However, to date, these molecules have marketing authorizations only in certain countries. For example, they do not have a marketing authorization in France.

Thus, no solution exists that is actually satisfactory for the prevention and/or treatment of cryptosporidiosis.

Chitin and chitosan are biocompatible, biodegradable, nontoxic compounds characterized by a strong negative charge. Chitin and chitosan are used in numerous very varied applications, ranging from food-processing to water treatment, and including analytical techniques, the cosmetics industry and the medical field (see Shahidi et al., Trends in Food Science & Technology, 1999, 10: 37-51).

By virtue of their antibacterial and antifungal properties, chitin and chitosan are in particular used as a preservative and in the manufacture of protective food films.

In the medical field, chitosan is, for example, used as an adjuvant in vaccines, a hemostatic agent, an anticoagulant, an antithrombogenic agent, a matrix for producing tissues (skin, bone, cartilage, liver, nerves, blood vessels), an agent for accelerating the healing of and for treating burns, a support for the transport, immobilization and encapsulation of molecules, such as for the controlled release of medicaments.

For example, Alvarez et al. (European Journal of Pharmaceutical Sciences, 2012, 47: 215-227) have tested, in vitro, the effect of microspheres based on chitosan and on polyvinyl alcohol which contain, as medicament, a complex of diloxanide furoate and cyclodextrins, on the infection of intestinal cells by *C. parvum*. The authors indicate that the adhesion of the microspheres to the intestinal cells in vitro could make it possible to inhibit the attachment of *C. parvum* to intestinal cells and serve as a medicament release system. However, the capacity of these microspheres to adhere to intestinal cells after administration in vivo is not demonstrated.

Thus, there is a real need for alternative solutions for preventing and/or treating parasitoses, and in particular cryptosporidiosis. Preferably, these alternative solutions have few or no toxic effects, are based on compounds of natural origin, the innocuousness of which in humans and/or animals is known, and are simple to prepare and use.

SUMMARY OF THE INVENTION

Generally, the present invention is based on the demonstration that, entirely originally, chitin or chitin derivatives used as sole active ingredient are effective in preventing and/or treating parasitoses.

The term "parasitosis" is intended to mean herein a disease associated with a protozoan, for example *Cryptosporidium* in the case of cryptosporidiosis.

A subject of the present invention is particularly chitin or chitin derivatives used as sole active ingredient in the prevention and/or treatment of cryptosporidiosis.

The invention also relates to original compositions combining chitin and/or a chitin derivative as active ingredient with one or more other compounds of natural origin, for treating and/or preventing parasitoses, and in particular cryptosporidiosis.

These original compositions according to the invention make it possible in particular to reduce mortality in young animals and/or diarrhea.

Furthermore, these compositions have the advantage of containing only compounds of natural origin, the innocuousness of which in humans and/or animals is known at the doses recommended for use.

These original compositions thus have few or no toxic effects.

The process for preparing these compositions is simple to carry out, requiring only simple mixing of the various compounds.

These original compositions also have the advantage of being able to be integrated into food compositions, whether they are solid or liquid.

A first subject of the invention thus relates to a composition comprising:
- at least one base agent chosen from chitin or a chitin derivative, and
- an agent for stimulating immunity and/or an antiparasitic agent, as secondary agents.

The chitin derivative is preferably chosen from chitosan, N-acetylglucosamine or glucosamine.

Preferred base agents are chitosan and N-acetylglucosamine.

The agent for stimulating immunity is preferably chosen from yeast hulls, a yeast extract, selenium, a microorganism, or combinations thereof.

The antiparasitic agent is chosen from an essential oil, active carbon, lauric acid, or combinations thereof.

A preferred antiparasitic agent comprises an essential oil.

Said composition may be a food composition, a food supplement or a pharmaceutical composition.

A second subject of the invention relates to a composition as defined above, for use as a medicament.

A third subject of the invention relates to chitin, a chitin derivative or a composition as defined above, for use as a medicament in the prevention and/or treatment of a parasitosis, preferably cryptosporidiosis, in particular in humans or animals.

A more detailed description of certain preferred embodiments of the invention is given below.

BRIEF DESCRIPTION OF THE DRAWINGS

FIG. 1 depicts a graph which represents the results of 2 independent experiments. The administration of walls induces a significant decrease ($p<0.01$) in oocysts in the two experiments. The administration of yeast hulls enables a significant decrease in oocysts excretion.

DETAILED DESCRIPTION

As previously indicated, the invention relates to compositions based on chitin and/or chitin derivatives used as an active ingredient and referred to herein as base agents.

These compositions may also comprise other compounds, preferably compounds of natural origin, referred to herein as secondary agents.

The secondary agents are chosen from an agent for stimulating immunity and an antiparasitic agent.

A subject of the present invention is thus a composition comprising:
  at least one base agent chosen from chitin or a chitin derivative, and
  an agent for stimulating immunity and/or an antiparasitic agent.

Chitin is a component that can be found, for example, in the exoskeleton of arthropods, the endoskeleton of cephalopods and the wall of fungi.

Chitin is a linear polysaccharide composed mainly of N-acetylglucosamine monomers linked to one another by β(1-4) linkages.

Chitin is generally obtained by means of a process comprising steps of deproteination and optionally demineralization of the cuticle or shell of crustacea, generally followed by a decoloration step.

The deproteination step is generally a basic treatment step (for example with sodium hydroxide, potassium hydroxide, sodium carbonate, potassium carbonate or sodium phosphate).

The demineralization step is generally an acidic treatment step (for example with hydrochloric acid, nitric acid, sulfuric acid, acetic acid or formic acid).

The decoloration step is for example carried out by treatment with an oxidizing agent.

Chitin has a degree of acetylation (DA) greater than 50%.

The degree of acetylation is the average number of N-acetylglucosamine units for 100 monomers.

It is also possible to use the degree of deacetylation (DDA) which is equal to 100−DA (as a percentage).

The term "chitin derivative" is intended to mean any compound which can be obtained from chitin, in particular by means of one or more hydrolysis, deacetylation, carboxymethylation, succinylation or acidification steps.

An example of a chitin derivative is chitosan.

Chitosan is a linear polysaccharide composed of glucosamine monomers and N-acetyl-glucosamine monomers which are randomly distributed and linked to one another by β(1-4) linkages.

Chitosan has a degree of acetylation (DA) of less than 50%.

The chitosan used in the compositions according to the invention preferably has a degree of acetylation of less than 40%, more preferentially less than 30%, even more preferentially less than 20%, for example less than or equal to 10%.

The chitosan can be obtained by chemical deacetylation (for example by treatment in a concentrated sodium hydroxide solution), thermochemical deacetylation or enzymatic deacetylation of chitin.

The chitosan thus obtained is generally insoluble in acidic aqueous solutions (in particular at a pH below 6).

It is possible to use methods well known to those skilled in the art to render the chitosan soluble in acidic aqueous solutions (in particular at a pH below 6).

For example, soluble chitosan can be obtained by treatment with hydrochloric acid.

A composition according to the invention may comprise soluble chitosan and/or insoluble chitosan.

In the context of the present invention, the insoluble or soluble nature of the chitosan is therefore determined by measuring its solubility in an acidic aqueous solution, in particular at a pH below 6.

In a preferred composition according to the invention, the chitosan used is a soluble chitosan.

Another example of a chitosan derivative is N-acetylglucosamine, also known as N-acetyl-D-glucosamine or NAG.

N-acetylglucosamine is, for example, obtained by complete hydrolysis of chitin or of chitosan, for example by enzymatic or acid hydrolysis, or else by N-acetylation of glucosamine.

Yet another example of a chitin derivative is glucosamine, also known as D-glucosamine.

Glucosamine is, for example, obtained by complete hydrolysis of chitosan, such as enzymatic or acid hydrolysis.

A subject of the present invention is particularly a composition as defined above, characterized in that the chitin derivative is chosen from chitosan, N-acetylglucosamine or glucosamine.

The chitin derivatives that are preferred for use in the compositions according to the invention are chitosan and N-acetylglucosamine.

A preferred composition according to the invention comprises a single base agent.

When the composition comprises just one base agent, the base agent is preferably chitosan or N-acetylglucosamine, more preferentially chitosan.

In one advantageous embodiment, the composition according to the invention comprises at least two base agents.

For example, another preferred composition according to the invention may comprise two base agents.

When the composition according to the invention comprises two base agents, these two base agents are preferably chitosan and N-acetylglucosamine.

In another embodiment of the invention, the composition comprises at least three base agents, for example three base agents, four base agents or more.

A preferred composition according to the invention comprises, as base agents, chitosan and optionally N-acetylglucosamine.

The agent for stimulating immunity is preferably a compound of natural origin or a combination of compounds of natural origin.

A subject of the present invention is thus particularly a composition as defined above, characterized in that the agent for stimulating immunity is chosen from yeast hulls, a yeast extract, selenium, a microorganism, or combinations thereof.

The agent for stimulating immunity may, for example, comprise a combination of:
  yeast hulls and yeast extract,
  yeast hulls and selenium,
  yeast hulls and microorganisms,
  yeast extract and selenium,
  yeast extract and microorganism,
  selenium and microorganism,
  yeast hulls, yeast extract and selenium,
  yeast hulls, yeast extract and microorganism,
  yeast hulls, selenium and microorganism,
  yeast extract, selenium and microorganism, and
  yeast hulls, yeast extract, selenium and microorganism.

The yeast hulls correspond to the insoluble fraction of yeasts, i.e. the yeast wall and the yeast plasma membrane.

A yeast extract corresponds to the soluble fraction of yeasts.

The yeast used to prepare the yeast hulls and/or the yeast extract is preferably chosen from the *Saccharomyces* genus, preferably *Saccharomyces cerevisiae, Saccharomyces pastorianus* or *Saccharomyces bayanus*; the *Torulaspora* genus, preferably *Torulaspora delbrueckii*; the *Lindnera* genus, for example *Lindnera jadinii*; and the *Kluyveromyces* genus, preferably *Kluyveromyces lactis* or *Kluyveromyces marxianus*.

A yeast which is preferred for preparing the yeast hulls and/or the yeast extract is *Saccharomyces cerevisiae*.

Conventionally, the yeast hulls or the yeast extract are obtained by means of a process comprising a step of yeast autolysis followed by a step of separation of the soluble fraction from the insoluble fraction, the isolated insoluble fraction corresponding to the yeast hulls and the soluble fraction corresponding to the yeast extract.

The insoluble fraction and/or the soluble fraction can then be dried.

In one advantageous embodiment, the yeast hulls are obtained according to a process comprising the following steps:
  production of yeasts in a fermenter so as to obtain a cream yeast,
  acidification of the cream yeast at a pH of between 1 and 5,
  autolysis at a temperature which is fixed or variable between 45° C. and 70° C., optionally in the presence of proteolytic enzymes,
  separation of the insoluble fraction corresponding to the yeast hulls (between 10% and 14% of dry matter),
  cooling to 4° C.,
  optionally, drying.

The yeast hulls may be in liquid form, in dry form or in viscous form. It is considered that they are in dry form when their dry matter content is at least 85%, preferably at least 90%, and even more preferentially at least 94% by weight. Conversely, if their dry matter content is less than 20% by weight, it is considered that they are in liquid form. Starting from 20% and below 85% by weight of dry matter, it is considered that the yeast hulls are in viscous form.

The yeast hulls comprise predominantly carbohydrates (between 40% and 60% of carbohydrates by weight of dry matter) consisting mainly of β-glucans and of mannans.

They also contain from 10% to 30%, in particular approximately 15% to 30%, of proteins by weight of dry matter.

The yeast hulls are preferably used in dry form.

In one advantageous embodiment, the yeast extract is obtained according to a process comprising the following steps:
  production of yeasts in a fermenter so as to obtain a cream yeast,
  acidification of the cream yeast at a pH of between 1 and 5,
  autolysis at a temperature which is fixed or variable between 45° C. and 70° C., optionally in the presence of proteolytic enzymes,
  separation of the soluble fraction corresponding to the yeast extract,
  cooling to 4° C.,
  optionally, drying.

The yeast extract may be in dry form, preferably in the form of a fine water-soluble powder, in liquid form or in paste form.

It is considered that the yeast extract is in dry form when its dry matter content is at least 85%, preferably at least 90%, and even more preferentially at least 94% by weight. If its dry matter content is less than 70% by weight, it is considered that it is in liquid form. Starting from 70% and below 85% by weight of dry matter, it is considered that the yeast extract is in paste form.

The yeast extract used is preferably in dry form, more preferentially in the form of a fine water-soluble powder.

A yeast extract comprises predominantly proteins, preferably at least 55% of proteins.

The selenium is selenium in mineral form or in organic form, preferably in organic form.

The selenium in organic form is, for example, in the form of selenomethionine, selenocysteine, selenoxide, S-(methylseleno)cysteine, Se-methylselenocysteine, Se-adenosylhomocysteine, selenolanthionine, selenocystine, selenocystathionine, γ-glutamyl-Se-methylselenocysteine, dimethylselenide, dimethyldiselenide, diethylselenide, (S)-2-amino-4-(methylselanyl)butanoic acid, R,S-2-hydroxy-4-methylselenobutanoic acid, or mixtures thereof.

The selenium in organic form is, for example, provided in the form of a selenium-enriched yeast, selenium totally or partially extracted from yeast, or combinations thereof.

A selenium-enriched yeast can be obtained by multiplication of yeasts in the presence of selenium.

Preferably, the selenium-enriched yeast is a *Saccharomyces cerevisiae* yeast.

The selenium-enriched yeast is preferably in the form of inactivated yeast, the yeast being for example inactivated by heat treatment.

The selenium-enriched yeast comprises, for example, at least 2000 mg of selenium per kg of dry matter, of which 97% to 99% of the selenium is in organic form and 63% of the total selenium is in the form of selenomethionine.

The selenium-enriched yeast is preferably used in powder form.

A subject of the present invention is thus particularly a compound as defined above, characterized in that the selenium is in the form of a selenium-enriched yeast, selenium totally or partially extracted from yeast, or combinations thereof.

In one preferred composition according to the invention, the selenium is in the form of a selenium-enriched yeast.

The microorganism which can be used in the compositions according to the invention is a bacterium or a yeast.

The microorganism is preferably chosen from a bacterium of the *Bacillus, Lactobacillus, Bifidobacterium, Enterococcus, Propionibacterium, Pediococcus* or *Lactococcus* genus, or a yeast of the *Saccharomyces* or *Kluyveromyces* genus, or combinations thereof.

A microorganism of the *Bacillus* genus is, for example, chosen from the species *Bacillus subtilis, Bacillus coagulans, Bacillus pumilus, Bacillus agglomerans, Bacillus clausii* or *Bacillus cereus*.

A microorganism of the *Lactobacillus* genus is, for example, chosen from the species *Lactobacillus johnsonii, Lactobacillus acidophilus, Lactobacillus reuteri, Lactobacillus rhamnosus, Lactobacillus casei, Lactobacillus paracasei, Lactobacillus plantarum, Lactobacillus delbrueckii, Lactobacillus brevis, Lactobacillus gasseri* or *Lactobacillus salivarius*.

A microorganism of the *Bifidobacterium* genus is, for example, chosen from the species *Bifidobacterium lactis, Bifidobacterium infantis, Bifidobacterium longum, Bifidobacterium bifidum, Bifidobacterium animalis, Bifidobacterium breve* or *Bifidobacterium adolescensis*.

A microorganism of the *Enterococcus* genus is, for example, the species *Enterococcus faecium*.

A microorganism of the *Propionibacterium* genus is, for example, chosen from the species *Propionibacterium freudenreichii, Propionibacterium acidipropionici* or *Propionibacterium jensenii*.

A microorganism of the *Lactococcus* genus is, for example, chosen from the species *Lactococcus lactis* or *Lactococcus thermophilus*.

A microorganism of the *Saccharomyces* genus is, for example, chosen from the species *Saccharomyces cerevisiae, Saccharomyces pastorianus* or *Saccharomyces bayanus*.

A microorganism of the *Kluyveromyces* genus is, for example, chosen from the species *Kluyveromyces lactis* or *Kluyveromyces marxianus*.

A microorganism of the *Pediococcus* genus is, for example, chosen from the species *Pediococcus acidilactici, Pediococcus dextrinicus* or *Pediococcus pentosaceus*.

In a preferred composition according to the invention, the microorganism is a bacterium of the *Bacillus* genus, more preferentially *Bacillus subtilis*.

In another preferred composition according to the invention, the microorganism is a bacterium of the *Lactobacillus* genus, more preferentially *Lactobacillus johnsonii*.

In yet another preferred composition according to the invention, the microorganism is a combination of a bacterium of the *Bacillus* genus and of a bacterium of the *Lactobacillus* genus, more preferentially a combination of *Bacillus subtilis* and *Lactobacillus johnsonii*.

The microorganism may be living or deactivated.

The term "deactivated" or alternatively "inactivated" is intended to mean a dead microorganism, i.e. a microorganism of which the metabolism is irreparably stopped.

A deactivated microorganism can be obtained by means of techniques well known to those skilled in the art, such as a heat treatment, a treatment consisting in subjecting the microorganism to several successive freezing and thawing cycles, an irradiation treatment, a spray-drying treatment, or a combination of these treatments.

Preferably, the composition according to the invention comprises a deactivated microorganism.

The antiparasitic agent is preferably a compound of natural origin or a combination of compounds of natural origin.

The antiparasitic agent is, for example, chosen from an essential oil, active carbon, lauric acid, or combinations thereof.

A preferred antiparasitic agent consists of an essential oil or a mixture of essential oils, and optionally active carbon and/or lauric acid.

An essential oil is a liquid with a high concentration of volatile aromatic compounds of a plant.

The term "essential oil" is synonymous with the term "plant essence".

The processes for obtaining an essential oil from a plant are well known to those skilled in the art.

The essential oil may, for example, be obtained by hydrodistillation, i.e. steam distillation, extraction with volatile solvents, cold-expression extraction or extraction with supercritical $CO_2$.

A subject of the present invention is in particular a composition as defined above, characterized in that the essential oil is chosen from garlic essential oil, citronella essential oil, cinnamon essential oil, thyme essential oil, oregano essential oil, tea tree essential oil, lemon essential oil, eucalyptus essential oil, or combinations thereof.

The garlic essential oil is rich in allicin and can be obtained from *Allium sativum*.

The citronella essential oil is rich in citral and citrannal and can be obtained from *Melissa officinalis*.

The cinnamon essential oil is rich in cinnamaldehyde and cinnamyl acetate and can be obtained from *Cinnamomum zeylanicum*.

The thyme essential oil is rich in thymol and can be obtained from *Thymus vulgaris*.

The oregano essential oil is rich in thymol and carvacrol and can be obtained from *Origanum vulgare*.

The tea tree essential oil is rich in gamma-terpinene, terpinen-4-ol and alpha-terpineol and can be obtained from *Melaleuca alternifolia*.

The lemon essential oil is rich in limonene and can be obtained from *Citrus limon*.

The eucalyptus essential oil is rich in 1,8-cineole and can be obtained from *Eucalyptus globulus* or *Eucalyptus radiata*.

Preferably, the antiparasitic agent comprises or consists of a mixture of at least two essential oils, preferably at least three essential oils, even more preferentially four essential oils.

In one particularly advantageous embodiment, the essential oil or the mixture of essential oils is encapsulated in yeast hulls.

The term encapsulated essential oil or encapsulated essential oil mixture is then used.

The processes for encapsulating oils in yeast hulls are well known to those skilled in the art (see, for example, document EP 0 242 135 or Normand et al., Journal of Agricultural and Food Chemistry, 2005, 53: 7532-7543).

Typically, the essential oil encapsulated in yeast hulls or the essential oil mixture encapsulated in yeast hulls is obtained by means of a step of contacting said essential oil or said essential oil mixture to be encapsulated in a suspension comprising the yeast hulls, followed by an optional drying step.

The yeast hulls used are as defined above.

They are preferentially *Saccharomyces cerevisiae* yeast hulls.

A subject of the present invention is more particularly a composition as defined above, characterized in that the antiparasitic agent comprises garlic essential oil, citronella essential oil, cinnamon essential oil and thyme essential oil.

In one preferred embodiment, the garlic, citronella, cinnamon and thyme essential oils are provided in the form of a mixture of these four essential oils.

Said mixture of garlic, citronella, cinnamon and thyme essential oils is preferably encapsulated in yeast hulls.

A mixture of essential oils that is preferred according to the invention comprises 3% to 7% of garlic essential oil, 7% to 13% of citronella essential oil, 59% to 69% of cinnamon essential oil, and 21% to 32% of thyme essential oil, the percentages being expressed by weight relative to the weight of the mixture.

In another advantageous embodiment, the above essential oil mixture is encapsulated in *Saccharomyces cerevisiae* yeast hulls and this encapsulated essential oil mixture comprises from 10% to 30% of essential oils by weight relative to the total weight, preferably 20% to 30% of essential oils by weight relative to the total weight.

Active carbon, also called activated carbon or activated vegetable carbon, is a black, light powder consisting essentially of carbon-based material with a porous structure, characterized by a very large specific surface area.

Active carbon can be produced from any carbon-rich plant organic matter by means of processes well known to those skilled in the art.

Lauric acid, also called dodecanoic acid, is a medium-chain fatty acid composed of 12 carbon atoms.

An example of a composition according to the invention comprises or consists of:
- chitosan and/or N-acetylglucosamine as base agents, preferably chitosan,
- an agent for stimulating immunity comprising or consisting of:
  - yeast hulls,
  - a yeast extract,
  - selenium, preferably in the form of a selenium-enriched yeast, and
  - optionally, a microorganism chosen from *Bacillus subtilis, Lactobacillus johnsonii, Saccharomyces cerevisiae* or combinations thereof,
- an antiparasitic agent comprising or consisting of:
  - thyme essential oil, citronella essential oil, cinnamon essential oil and garlic essential oil, preferably in the form of an encapsulated essential oil mixture,
  - optionally, active carbon, and
  - optionally, lauric acid.

A preferred composition according to the invention comprises or consists of:
- 2% to 15% of chitosan, preferably from 4% to 10% of chitosan, more preferentially from 6% to 10% of chitosan, and/or 2% to 30% of N-acetylglucosamine, preferably from 2% to 20% of N-acetylglucosamine, more preferentially from 4% to 10% of N-acetylglucosamine, as base agents (preferably chitosan and optionally N-acetylglucosamine),
- an agent for stimulating immunity comprising or consisting of:
  - 25% to 85% of yeast hulls, preferably from 30% to 70% of yeast hulls, more preferably from 40% to 60% of yeast hulls,
  - 1% to 15% of a yeast extract, preferably from 2% to 10% of a yeast extract, more preferentially from 2% to 5% of a yeast extract,
  - 0.002% to 0.02% of selenium, preferably from 0.004% to 0.01% of selenium, more preferentially from 0.004% to 0.006% of selenium, or else from 1% to 10% of selenium-enriched yeast, preferably from 2% to 5% of selenium-enriched yeast, more preferentially from 2% to 3% of selenium-enriched yeast,
  - optionally from $10^5$ CFU to $10^{12}$ CFU for 100 g of composition of a microorganism chosen from *Bacillus subtilis, Lactobacillus johnsonii, Saccharomyces cerevisiae* or combinations thereof, preferably from $10^5$ CFU to $10^{11}$ CFU, preferably from $10^5$ CFU to $10^{10}$ CFU, preferably from $10^6$ CFU to $10^9$ CFU, more preferentially from $10^6$ CFU to $10^8$ CFU,
- an antiparasitic agent comprising or consisting of:
  - 0.4% to 20% of essential oil, preferably from 0.4% to 12%, more preferentially from 1% to 6%, even more preferentially from 1.5% to 4%, the essential oil preferably being in the form of an encapsulated thyme, citronella, cinnamon and garlic essential oil mixture, or else 2% to 65% of encapsulated essential oil, preferably from 2% to 40%, more preferentially from 5% to 20%, even more preferentially from 8% to 12%, the encapsulated essential oil preferably being in the form of an encapsulated thyme, citronella, cinnamon and garlic essential oil mixture,
  - optionally 2% to 25% of active carbon, preferably 4% to 15%, more preferentially 4% to 8%, and
  - optionally 5% to 40% of lauric acid, preferably 5% to 30%, more preferentially 6% to 20%.

The percentages are expressed in g for 100 g of composition.

One CFU corresponds to one colony-forming unit.

In the above compositions, the percentages of yeast hulls do not comprise the optional yeast hulls used as encapsulating agent for encapsulating the essential oils.

The compositions according to the invention are obtained by means of a simple step of mixing the various constituents thereof, optionally followed by a drying step.

Generally, the mixture of the various constituents gives a composition in dry form, without requiring a subsequent drying step.

The compositions as defined above are preferably in dry form, in particular in powder form.

The compositions according to the invention may also be in liquid form.

The liquid compositions are generally obtained by dissolving a composition as defined above in dry form.

Compositions according to the invention are, for example, the compositions A, B, C and D described in example 3.

A subject of the present invention is also a composition as defined above, characterized in that said composition is a food composition, a food supplement or a pharmaceutical composition.

The food composition may be a composition intended for feeding humans or animals.

A food composition denotes any type of food, drink or confectionery product.

When the food composition is intended for feeding humans, the food composition may, for example, be a drink, a cereal bar, a chewing gum, chocolate, a dairy product, such as a fermented dairy product, or a fermented product of vegetable origin.

Preferably, the food composition is intended for animals.

A food composition intended for animals may, for example, also comprise a compound chosen from whey, milk powder, whey proteins, corn gluten feed, soybean cake, a premix of minerals and vitamins, and an oil, for example palm or coconut oil.

The food composition intended for animals is, for example, drinking water, colostrum or milk, in particular a milk suitable for the animal and its age.

The term "food supplement" denotes a food product, the purpose of which is to supplement the normal diet.

A food supplement constitutes a concentrated source of nutrients or of other substances which have a nutritional or physiological effect, alone or in combination.

A food supplement is sold in dose form, namely the presentation forms such as a gel capsule, lozenge, tablet, pill and other similar forms, sachet of powder, vial of liquid, bottle equipped with a dropper and other analogous forms of liquid or powdered preparations intended to be taken in measured units of low amount.

A pharmaceutical composition according to the invention is preferably intended for oral administration.

By way of example of a composition which is in a form suitable for the oral route, mention may be made of a tablet, a capsule, a gel capsule, a sachet, a powder, a cream, a syrup, a paste, a gel or a vial.

The pharmaceutical composition may be administered as a mixture with a solid or liquid food (for example milk in young animals).

A pharmaceutical composition may comprise, in addition to the base agent(s) and to the secondary agent(s), at least one physiologically acceptable carrier or excipient.

A physiologically acceptable carrier or excipient may be a carrier or excipient which is suitable for administration in humans and/or in animals.

The carrier or excipient is, for example, chosen from those conventionally used which are suitable for the preparation of oral forms.

A pharmaceutical composition according to the present invention may also comprise at least one additional pharmaceutical active ingredient (i.e., in addition to the base agent(s) and to the secondary agent(s)).

The term "pharmaceutical active ingredient" is intended to mean any compound or substance of which the administration has a therapeutic effect or a beneficial effect on the health or general condition of a patient or of a subject to whom it is administered.

Thus, an additional pharmaceutical active ingredient may be active against cryptosporidiosis and/or the associated clinical signs, such as diarrhea, dehydration, weakness, loss of appetite and colic.

Examples of pharmaceutical active ingredients which may be present in a composition of the present invention include, without limitation, cryptosporidiostatic agents, anti-inflammatories, antibiotics, antipyretic agents, anti-emetic agents, antihistamines, vitamins, antispasmodic agents, etc.

In one advantageous embodiment, the pharmaceutical composition according to the invention does not contain an additional pharmaceutical active ingredient acting directly against *Cryptosporidium*, such as, for example, a cryptosporidiostatic agent.

In another advantageous embodiment, the pharmaceutical composition according to the invention does not contain an additional pharmaceutical active ingredient.

The pharmaceutical composition according to the present invention may be administered using any combination of dosage and of route of administration that is effective for obtaining the desired therapeutic effect.

The exact amount to be administered can vary from one patient or from one animal to another, depending on age, weight, the general condition thereof, and the type of preventive or curative treatment.

A subject of the present invention is also a composition as defined above, for use as a medicament.

In particular, a subject of the present invention is a composition as defined above, for use as a medicament in the prevention and/or treatment of a parasitosis.

As previously indicated, it is the first time that the use of chitin or chitin derivatives as sole active ingredient is described in the prevention and/or treatment of parasitoses, and in particular in the prevention and/or treatment of cryptosporidiosis.

Thus, a subject of the present invention is also chitin and/or a chitin derivative for use as a medicament in the prevention and/or treatment of a parasitosis.

A subject of the present invention is more particularly chitin, a chitin derivative or a composition as defined above, for use as a medicament in the prevention and/or treatment of a parasitosis, characterized in that the parasitosis is cryptosporidiosis.

The microorganism responsible for cryptosporidiosis is *Cryptosporidium*, preferably chosen from the species *C. parvum, C. bovis, C. ryanae, C. andersoni, C. cervine, C. hominis, C. meleagridis, C. felis, C. muris, C. suis, C. baileyi* and *C. canis*.

The chitin derivative is as defined above.

The chitin derivative for use as a medicament in the prevention and/or treatment of a parasitosis is preferably chosen from chitosan, N-acetylglucosamine or glucosamine.

A subject of the present invention is particularly chitin, a chitin derivative or a composition as defined above, for use as a medicament in the prevention and/or treatment of a parasitosis, preferably cryptosporidiosis, in humans or animals.

The prevention and/or treatment of cryptosporidiosis in animals concerns quite particularly ruminants, in particular cattle, the ovine race, members of the goat family and cervidae, and also pigs, poultry and rabbits.

The prevention and/or treatment of cryptosporidiosis in animals concerns quite particularly young animals, such as calves, kids and lambs.

In one advantageous embodiment, a subject of the present invention is chitin, a chitin derivative or a composition as defined above, for use as a medicament in the prevention and/or treatment of a parasitosis, preferably cryptosporidiosis, in humans or animals, the administration of the chitin, of the chitin derivative or of the composition being carried out during the colostral phase.

When the composition is administered during the colostral phase, said composition preferably comprises no living bacterium, and more generally no living microorganism.

A subject of the present invention is also a method for preventive or curative treatment of cryptosporidiosis, comprising a step of administering, to the sick human or animal subject, chitosan, a chitosan derivative, or a composition as defined above.

The daily dosage depends on the human or the animal, the age thereof and the type of preventive or curative treatment.

By way of example, the daily dosage in humans corresponds to an administration of 10 g to 25 g of the composition according to the invention, preferably of 15 g to 20 g of the composition.

The daily dose can be administered in one, two or three intakes.

Likewise by way of example, the daily dosage in animals may be:
- 2 g to 10 g of the composition according to the invention per day, for 7 consecutive days for an animal with a live weight of 3 kg to 5 kg,
- 5 g to 15 g of the composition according to the invention per day, for 7 consecutive days for an animal with a live weight of 30 kg to 50 kg,
- 10 g to 20 g of the composition according to the invention per day, for 7 consecutive days for an animal with a live weight of greater than 50 kg.

At the doses tested, no side effect of the compositions according to the invention was observed on the animals.

Other features and advantages of the invention will emerge more clearly on reading the following implementation examples which illustrate the invention without limiting it, and for the understanding of which reference will be made to the appended drawings.

Example 1: Inhibition of *C. Parvum* In Vitro Multiplication

Experiments carried out in collaboration with the "parasites transmis par les aliments" ["food-transmitted parasites"] team of the Unité Mixte de Recherche [Mixed Research Unit] Biologie moléculaire et Immunologie Parasitaire et fongique (BIPAR) [Molecular biology and parasitic and fungal immunology], at the Alfort Ecole Nationale Vétérinaire [National Veterinary School].

Materials and Methods
(i) Cell Lines

Two cell models were tested: HCT-8 cells (human ileocecal adenocarcinoma cells) and Caco-2 cells (human colonic adenocarcinoma cells).
(ii) Compounds Tested: chitosan, NAG, paromomycin The soluble chitosan is chitosan hydrochloride with a degree of deacetylation greater than or equal to 90% and a degree of viscosity of 5.5 mPas (dynamic viscosity measured at 20° C. in a 0.5% distilled water solution) (Kraeber & Co GMBH, Germany).

The NAG (N-acetylglucosamine) comes from Kraeber & Co GMBH, Germany.

The paromomycin (paromomycin sulfate 100%, Antibioticos SPA, Italy) is an antimicrobial medicament used in the treatment of cryptosporidiosis which makes it possible to reduce oocyst excretion.
(iii) *C. parvum*

The Iowa *Cryptosporidium parvum* strain (Waterborne inc., New Orleans, La., USA) is used for the tests.
(iv) Cell Infection The infection is carried out on cells at 70%-80% confluence, cultured in a monolayer on collagen-coated coverslips in 24-well plates.

The supernatant of the cells in a monolayer is replaced with 3 ml of culture medium to which $1 \times 10^4$ *C. parvum* oocysts are added. After incubation for 3 hours in a humid incubator at 37° C. and 5% $CO_2$, the supernatant is replaced with 3 ml of culture medium and incubated for 48 h in a humid incubator at 37° C., 5% $CO_2$ and 80% humidity.

(v) Preincubation Test

In each well of a plate, $1 \times 10^4$ oocysts are brought into contact with 500 µg/ml of paromomycin, chitosan or NAG.

The plates are incubated for 24 h in a humid incubator at 37° C. and 5% $CO_2$.

The cells are then infected as indicated above.
(vi) Direct Test

The culture medium of the infected cells is replaced with 1 ml of culture medium to which the test compound is then added, at a final concentration of 500 µg/ml.

The plates are incubated for 48 h in a humid incubator at 37° C. and 5% $CO_2$.
(vii) Staining and Counting of the Intracellular Oocysts The intracellular oocysts are stained after fixing the cells with methanol. The labeling is carried out using a specific conjugated polyclonal antibody (Sporo-Glo 20×Waterborne inc., New Orleans, La., USA). The coverslips are then mounted on slides. The intracellular oocysts are counted with a fluorescence microscope.

On each slide, 6×50 fields randomly chosen over the entire surface area of the slide are counted.
(viii) Statistical Analysis The results obtained are a triplicate mean. The data are analyzed by ANOVA. A p-value of less than or equal to 0.05 is considered to be significant.

Results
(i) Cytotoxicity

Preliminary tests made it possible to determine the optimum doses tolerated by the HCT-8 and Caco-2 cells and led to the dose of 500 µg/ml being chosen for testing each of the compounds.
(ii) Effect of the Preincubation of the Tested Compounds with the *C. parvum* Oocysts Before Infection The tested compounds are incubated for 24 h with *C. parvum* oocysts before the in vitro infection at a dose of 500 µg/ml.

The results obtained are given in table 1 for the HCT-8 cells and table 2 for the Caco-2 cells.

The paromomycin is capable of significantly inhibiting the development of the parasite both on the HCT-8 cells and on the Caco-2 cells (p<0.001): paromomycin reduces the parasite development by 99.5% on the HCT-8 cells and by 97.1% on the Caco-2 cells.

The same is true for chitosan and NAG.

The soluble chitosan reduces the parasite development respectively by 95.7% on the HCT-8 cells and by 97.6% on the Caco-2 cells (p<0.001).

The NAG reduces the parasite development respectively by 99.0% on the HCT-8 cells and by 97.4% on the Caco-2 cells (p<0.001).

TABLE 1

| Test | HCT-8 cells | Number of sporozoites | Mean | Standard deviation | % of viable sporozoites |
|---|---|---|---|---|---|
| 1 | T+ | 1040 | 1046 | 10.68 | 100 |
| 2 | T+ | 1037 | | | |
| 3 | T+ | 1061 | | | |
| 4 | Paromomycin | 3 | 6 | 2.49 | 0.53 |
| 5 | Paromomycin | 9 | | | |
| 6 | Paromomycin | 5 | | | |
| 7 | NAG | 12 | 11 | 2.49 | 0.99 |
| 8 | NAG | 14 | | | |
| 9 | NAG | 7 | | | |
| 10 | chitosan | 47 | 47 | 6.24 | 4.3 |
| 11 | chitosan | 52 | | | |

TABLE 1-continued

| Test | HCT-8 cells | Number of sporozoites | Mean | Standard deviation | % of viable sporozoites |
|---|---|---|---|---|---|
| 12 | chitosan | 37 | | | |
| 13 | T− | 0 | 0 | 0 | 0 |

T+: infected cells/
T−: noninfected cells

TABLE 2

| Test | Caco-2 cells | Number of sporozoites | Mean | Standard deviation | % of viable sporozoites |
|---|---|---|---|---|---|
| 1 | T+ | 844 | 1146 | 298.7 | 100 |
| 2 | T+ | 1553 | | | |
| 3 | T+ | 1042 | | | |
| 4 | Paromomycin | 23 | 33 | 12.97 | 2.87 |
| 5 | Paromomycin | 51 | | | |
| 6 | Paromomycin | 24 | | | |
| 7 | NAG | 21 | 30 | 9.0 | 2.61 |
| 8 | NAG | 39 | | | |
| 9 | NAG | 31 | | | |
| 10 | chitosan | 19 | 28 | 10.8 | 2.44 |
| 11 | chitosan | 40 | | | |
| 12 | chitosan | 25 | | | |
| 13 | T− | 0 | 0 | 0 | 0 |

T+: infected cells/
T−: noninfected cells (iii) Effect of the Tested Compounds on *C. parvum* Development During Direct Addition to the Infected Cells The various compounds are tested at a dose of 500 µg/ml.

The results are given in tables 3 (HCT-8 cells) and 4 (Caco-2 cells).

TABLE 3

| Test | HCT-8 cells | Number of sporozoites | Mean | Standard deviation | % of viable sporozoites |
|---|---|---|---|---|---|
| 1 | T+ | 393 | 345 | 37.6 | 100 |
| 2 | T+ | 342 | | | |
| 3 | T+ | 301 | | | |
| 4 | Paromomycin | 178 | 191 | 12.6 | 55.4 |
| 5 | Paromomycin | 187 | | | |
| 6 | Paromomycin | 208 | | | |
| 7 | NAG | 172 | 134 | 29.9 | 11.6 |
| 8 | NAG | 131 | | | |
| 9 | NAG | 99 | | | |
| 10 | chitosan | 90 | 73 | 11.8 | 6.4 |
| 11 | chitosan | 66 | | | |
| 12 | chitosan | 64 | | | |
| 13 | T− | 0 | 0 | 0 | 0 |

T+: infected cells/
T−: noninfected cells

Paromomycin, NAG and chitosan induce a significant reduction in parasite development in the two cell lines ($p<0.005$):

respectively of 44.6%, 88.4% and 93.6% on the HCT-8 cells, and respectively of 33.6%, 35.2% and 68% on the Caco-2 cells.

Thus, NAG and chitosan are more effective than paromomycin on the HCT-8 cells, and chitosan is more effective on the Caco-2 cells.

TABLE 4

| Test | Caco-2 cells | Number of sporozoites | Mean | Standard deviation | % of viable sporozoites |
|---|---|---|---|---|---|
| 1 | T+ | 774 | 881 | 79.0 | 100 |
| 2 | T+ | 908 | | | |
| 3 | T+ | 962 | | | |
| 4 | Paromomycin | 318 | 592 | 193.4 | 66.4 |
| 5 | Paromomycin | 782 | | | |
| 6 | Paromomycin | 675 | | | |
| 7 | NAG | 656 | 571 | 85.5 | 64.8 |
| 8 | NAG | 485 | | | |
| 9 | NAG | 337 | | | |
| 10 | chitosan | 372 | 282 | 70.8 | 32.0 |
| 11 | chitosan | 199 | | | |
| 12 | chitosan | 276 | | | |
| 13 | T− | 0 | 0 | 0 | 0 |

T+: infected cells/
T−: noninfected cells

Example 2: *C. Parvum* Adhesion or Replication in Enterocytes In Vitro

Materials and Methods (i) Cell Lines Tested and Oocysts

The *C. parvum* oocysts used were isolated from feces (stools) of calves that had been experimentally infected (by INRA [French National Institute for Agricultural Research] of Tours).

The tests are carried out on cells of the CMT-93 murine line (mycoplasma-free) cultured in complete medium comprising 10% of FCS (Fetal Calf Serum).

(ii) Compounds Tested

The insoluble chitosan is poly-(N-deacetyl-D-glucosamine) with a dry matter content of 6.43% and a degree of deacetylation of 95.5% (Federal Laboratories Chemical Corp, NY, USA).

The soluble chitosan is chitosan hydrochloride with a degree of deacetylation greater than or equal to 90% and a degree of viscosity of 5.5 mPas (dynamic viscosity measured at 20° C. in a 0.5% distilled water solution) (Kraeber & Co GMBH, Germany).

The NAG (N-acetylglucosamine) comes from Kraeber & Co GMBH, Germany.

The following are also tested:
yeast hulls (Safmannan, Lesaffre),
a selenium-enriched yeast (Selsaf, Lesaffre),
active carbon,
garlic essential oil,
a mixture of essential oils (comprising 6% of garlic essential oil, 10% to 13% of citronella essential oil, 59% to 72% of cinnamon essential oil, and 23% to 32% of thyme essential oil),
a live *Saccharomyces cerevisiae* yeast (Actisaf, Lesaffre).

Interferon-γ at 10 ng/ml is used as a positive control. This is because partial inhibition of *C. parvum* multiplication in enterocytes under the action of this cytokine has been described.

(iii) Test of the Effect of the Compounds on *C. parvum* Development

The cells of the CMT-93 line are seeded in a proportion of $3.6 \times 10^5$ cells per well.

The test compounds are added after 8 h. After incubation for 16 h, an infection is then carried out with *C. parvum* oocysts (ratio of 5 oocysts/cell) in the presence of the compounds tested, at the selected doses which do not affect cell viability by more than 15%.

After 24 h, the cells are lysed with trypsin and labeled with a fluorescent lectin (VVL-FITC), in order to be able to find the infected cells with a fluorescence microscope. The number of infected cells is found manually. This technique is more laborious, but proved to be more accurate than counting the parasite-infected cells by cytometry.

Results

The soluble chitosan and the NAG tested at 18 µg/ml reduce parasite multiplication by 31% and 43%, respectively, in the cells of the CMT-93 line compared with the nontreated control.

These reductions are similar to that observed for the positive control, interferon-γ.

The insoluble chitosan tested at 18 µg/ml enables a smaller reduction of parasite multiplication, with approximately 40% of infected cells compared with 50% of infected cells for the nontreated control.

The active carbon at the dose of 18 µg/ml reduces parasite multiplication by 36% compared with the nontreated control. At this dose, the effect of the carbon remains similar to interferon-γ.

The mixture of essential oils (comprising 6% of garlic essential oil, 10% to 13% of citronella essential oil, 59% to 72% of cinnamon essential oil, and 23% to 32% of thyme essential oil) at the dose of 3.3 µg/ml or 30 µg/ml also enables a 30% reduction of parasite multiplication compared with the nontreated control, and similar to that observed for interferon-γ.

No effect is observed with the other compounds at the doses tested on parasite multiplication.

Example 3: Immune Response of Epithelial Cells and of Dendritic Cells (i) Cell Lines Tested and Oocysts The *C. parvum* oocysts used were isolated from feces (stools) of calves that had been experimentally infected (by INRA [French National Institute for Agricultural Research] of Tours).

The tests are carried out on cells of the CMT-93 murine line (mycoplasma-free) cultured in complete medium comprising 10% of FCS (Fetal Calf Serum) or on dendritic cells derived from bone marrow (immature) in the presence of GM-CSF (Granulocyte Macrophage Colony Stimulating Factor) added regularly to the culture for 9 days.

(ii) Compounds Tested

The products tested on the epithelial cells are:
NAG (N-acetylglucosamine) (Kraeber & Co GMBH, Germany).
yeast hulls (Safmannan, Lesaffre),
a live *Saccharomyces cerevisiae* yeast (Actisaf, Lesaffre),
an inactivated *Lactobacillus johnsonii* strain.

The products tested on the dendritic cells are:
yeast hulls (Safmannan, Lesaffre),
a live *Saccharomyces cerevisiae* yeast (Actisaf, Lesaffre),
a *Bacillus subtilis* strain,
a live *Lactobacillus johnsonii* strain,
an inactivated *Lactobacillus johnsonii* strain,
an *E. coli* strain.

(iii) Epithelial and dendritic cell immune response test

Epithelial cells

Chemokine production by the epithelium or other intestinal cells is important for the recruitment of the inflammatory cells required for protection against cryptosporidiosis in newborns. Chemokine production by epithelial cells is measured by quantitative RT-PCR (quantification by incorporation of Sybr green) after incubation of CMT-93 cells with the various compounds for 24 h.

Dendritic Cells

The tests are carried out on dendritic cells derived from bone marrow (immature) in the presence of GM-CSF (Granulocyte Macrophage Colony Stimulating Factor) added regularly to the culture for 9 days.

The production of the cytokine IL-12p40 is measured by ELISA 24 h after addition of the products of various dilutions. An antibiotic is added 4 h after the inoculation of the live products.

Results

For the epithelial cells, chemokines (CXCL2, CCL3, CCL20, CXCL10, CCL2) capable of attracting mononuclear phagocytes are produced by the epithelial cells in vitro in response to the compounds tested, but in a lesser amount than with the parasite infection. The NAG product is often found to be the most effective for CXCL10 and CCL20, then the yeast hulls, and the live yeast (Actisaf) for CCL3.

For the dendritic cells, the yeast hulls, the *Bacillus subtilis* strain, the lactobacilli, *E. coli*, and the live yeast all induce very strong IL-12p40 productions.

This experiment was reproduced on macrophages differentiated in vitro (in the presence of M-CSF for 6 days) and a very strong response is obtained for the lactobacilli and also the live yeast.

Example 4: Treatment of Cryptosporidiosis Induced in Kids

Materials and Methods

Kid Model (i) Compositions Tested

| Compounds | Trial 1 Composition A 2.5 g, 5 g or 10 g/kid/ meal * | Trial 2 Composition B 5 g/kid/ meal * | Trial 2 Composition C 7.5 g/kid/ meal * | Trial 2 Composition D 5 g/kid/ meal * |
|---|---|---|---|---|
| Yeast hulls | 70% | 76% | 51% | 38% |
| Yeast extract | 3% | 3% | 2% | 2% |
| Selenium-enriched yeast | 3% | 3% | 2% | 2% |
| Live yeast | 0% | 0% | 33% | 50% |
| NAG | 6% | 0% | 0% | 0% |
| Chitosan | 6% (soluble) | 8% (insoluble) | 5% (insoluble) | 4% (insoluble) |
| Active carbon | 6% | 0% | 0% | 0% |
| Mixture of essential oils | 6% | 10% | 7% | 5% |

* The kids are fed twice a day.

The yeast hulls are the product Safmannan (Lesaffre).
The yeast extract is the product EXL2020 (Biospringer).
The selenium-enriched yeast is the product Selsaf (Lesaffre).
The live yeast corresponds to the strain deposited on Dec. 2, 2010 at the Collection Nationale de Cultures de Microorganismes [National Collection of Microorganism Cultures] (CNCM, Institut Pasteur, 25 Rue du Docteur Roux, F-75724 PARIS Cedex 15) under number I-4407 (Actisaf, Lesaffre, at 9×10$^9$ CFU/g).

The mixture of essential oils comprises 6% of garlic essential oil, 10% to 13% of citronella essential oil, 59% to 72% of cinnamon essential oil and 23% to 32% of thyme essential oil.

The NAG comes from Kraeber & Co GMBH, Germany.

The soluble chitosan is chitosan hydrochloride with a degree of deacetylation greater than or equal to 90% and a degree of viscosity of 5.5 mPas (dynamic viscosity measured at 20° C. in a 0.5% distilled water solution) (Kraeber & Co GMBH, Germany).

The insoluble chitosan is a chitosan with a degree of deacetylation greater than 90% (Federalabs, United States).

The compositions A, B, C and D are in powder form.

(ii) Trial 1

The kids are divided up into 4 groups of 11 kids 2 to 4 days old:
  Group 1: Infected control not receiving treatment
  Group 2: 2.5 g of the composition A per kid, twice a day
  Group 3: 5 g of the composition A per kid, twice a day
  Group 4: 10 g of the composition A per kid, twice a day.

It should be noted that the kids were all treated metaphylactically with marbofloxacin by subcutaneous injection at a dose of 0.1 ml/kg once a day, owing to pneumonia lesions detected in dead kids before the dividing up into the 4 groups. This treatment does not interfere with the clinical trial since marbofloxacin is not effective against cryptosporidiosis. The kids are experimentally infested orally using a syringe at a dose of $10^6$ *Cryptosporidium parvum* oocysts (Waterborne Inc, New Orleans, USA) resuspended in water.

The dispensing of the composition A is carried out after suspending in 100 ml of milk (Optiprim whole milk replacer from the Sofivo group). The composition is dissolved extemporaneously, just before dispensing.

The mixture is dispensed individually, with a bottle, in the interests of convenience, each kid receiving 100 ml of mixture.

The treatment is dispensed in the morning and evening for 14 days and the administration began half a day before the experimental infestation. The dispensing of the treatment takes place before the meal in order to guarantee a better intake of the treatment.

(iii) Trial 2

The kids are divided up into 4 groups of 11 kids 2 to 4 days old:
  Group 1: Infected control not receiving treatment
  Group 2: 5 g of the composition B per kid, twice a day
  Group 3: 7.5 g of the composition C per kid, twice a day
  Group 4: 5 g of the composition D per kid, twice a day.

The kids are experimentally infested orally using a syringe at a dose of $10^6$ *Cryptosporidium parvum* oocysts (Waterborne Inc, New Orleans, USA) resuspended in water.

The dispensing of the compositions B, C and D is carried out after suspending in 100 ml of milk (Optiprim whole milk replacer from the Sofivo group). The composition is dissolved extemporaneously, just before dispensing.

The mixture is dispensed individually, with a bottle, in the interests of convenience, each kid receiving 100 ml of mixture.

The treatment is dispensed in the morning and evening for 14 days and the administration began half a day before the experimental infestation. The dispensing of the treatment takes place before the meal in order to guarantee a better intake of the treatment.

(iv) Measurements and Data Collection

Fecal matter is sampled daily from each kid in order to measure individual excretion by the Heine semi-quantitative method. The samples are taken in the rectum.

An excretion grade is assigned for each kid:
  0=no oocyst
  1=less than 1 oocyst
  2=1 to 10 oocysts
  3=11 to 20 oocysts
  4=21 to 30 oocysts
  5=31 to 40 oocysts.

A diarrhea grade ranging from 0 to 2 is assigned to each kid:
  0=no diarrhea,
  1=pasty diarrhea and
  2=liquid diarrhea.

The oocyst excretion and also the diarrhea grade reflect the effectiveness of the tested composition on the parasite. A decrease in excretion makes it possible to reduce the infestation pressure, which is generally accompanied by a score approaching zero. They are therefore advantageous from an epidemiological point of view.

(v) Statistical Analyses

The results are analyzed using the Statistica software. $Chi^2$, ANOVA, repeated measures ANOVA, Goodman gamma coefficient and Kruskal-Wallis tests are used.

Results (i) Trial 1

Distribution of the Groups

This trial was carried out with kids of multiple origins, which presents various drawbacks: variable microbism according to origin (pasteurellosis, colibacillosis), kids of different breed (without effect on cryptosporidiosis) and of different build (potential effect on the ability to survive the clinical episode).

Each group comprised 11 kids at the beginning of the experiment.

Validation of the Experimental Infection

The infection was conclusive since virtually 100% of the kids excreted oocysts 4 days after the infection. The kids of the livestock 1 began to excrete oocysts as early as the day after the infection, which attest to an infection in the livestock, prior to their arrival in the animal house. The kids of the control group originating from the livestocks 2 and 3 began to excrete oocysts 3 days after the experimental infection. 100% of the control kids excreted oocysts 4 days after the infection (average age of the kids: 8 days) and for 4 days.

Evolution of the Excretion

The evolution of the excretion is similar between the control group and the treated groups 2, 3 and 4.

Average Diarrhea Grade

In the control group 1, the average diarrhea score increased starting from the age of 7 days and began to decrease after 15 days in parallel with excretion.

In the groups 3 and 4, a decrease in the average diarrhea score over the maximum period of diarrhea was observed.

The average diarrhea period in the live animals is shorter in the groups 3 and 4 than in the control group 1.

The kids of the group 3 presented signs of diarrhea later than the other groups and at a lower level.

Morbidity

The morbidity was calculated as the percentage of kids exhibiting diarrhea (diarrhea scores 1 or 2) relative to the total number of kids present.

In the control group 1, more than 60% of the kids exhibited diarrhea between 8 and 15 days concomitantly with increased oocyst excretion.

The level of morbidity of the group 4 is lower than that in the other groups.

Moreover, the delay in the appearance of diarrhea in the group 3 is longer: while more than 60% of the kids of the groups 2 and 4 exhibit diarrhea from the age of 8 days, this percentage is reached only at the age of 11 days in the group 3.

Mortality 21 kids died "naturally" and 3 were euthanized on compassionate grounds. The age of the dead kids at the time of death was 5 to 17 days. The majority of them exhibited oocyst excretion, diarrhea and microscopic signs at the time of the autopsy which are compatible with cryptosporidiosis. Some of the kids did not die from cryptosporidiosis in this trial.

No major effect of the administration of the compositions could be noted.

Conclusion

In this trial, the transportation to and the arrival at the animal house were probably poorly tolerated by the kids already weakened by the circulation in the livestock of pathogenic agents responsible for pulmonary diseases, and 5 kids died before the dividing up into batches. This may explain why the results of the compositions according to the invention are less spectacular than expected.

However, the composition A had a beneficial effect on the diarrhea and the morbidity of the kids compared with those of the nontreated group.

The dose of 5 g per kid administered twice a day gave the best results.

(ii) Trial 2

Distribution of the Groups

This trial 2 was carried out with kids from one and the same origin, which as a result were very homogeneous in terms of age and weight and had no intercurrent pathological conditions. The extreme sensitivity of the kids to the experimental infection confirms the absence of prior infection by cryptosporidia. Each group comprised 11 kids at the beginning of the trial.

Validity of the Experimental Infection

All of the kids of the control group 1 excreted *C. parvum* oocysts massively from the age of 8 days (average excretion grade: 4.5 on a scale of 0 to 5), that is to say 4 days after the experimental infection. The only surviving kid of the control group 1 excreted oocysts continuously for 8 days.

Evolution of the Excretion

The evolution of the oocyst excretion was comparable in the groups 2, 3 and 4 receiving respectively the compositions B, C and D.

The highest average of the excretia grades in the groups 2, 3 and 4 was lower than that of the control group.

The average excretion was lower in the group 3 between 8 and 15 days than in the control group 1 and the groups 2 and 4.

Average Diarrhea Grade

Diarrhea appeared earlier in the groups 2, 3 and 4 than in the control group 1, in particular in the group 3 where more than 35% of the kids had diarrhea before 6 days. The episode of diarrhea due to cryptosporidiosis was then similar between the groups 2, 3 and 4 and the control group 1.

It should be noted that the interpretation of the comparison with the control group beyond 13 days was made impossible by the presence of a single surviving kid in the control group.

The percentage of kids with diarrhea was slightly lower in the groups 2, 3 and 4 compared with the control group 1.

The highest average of the diarrhea grades was much lower in the groups 2, 3 and 4 (respectively 1.7, 1.7 and 3.7) compared with the control group (4.5).

The duration of the diarrhea in the live kids was reduced in the groups 2, 3 and 4 compared with the control group.

Between 12 and 18 days of age, the diarrhea grades are significantly ($p<0.005$) higher in the group 1 than in the group 2; between 16 and 17 days, they are higher in the group 1 than in the group 3; and between 17 and 18 days, they are higher in the group 1 than in the group 4.

Morbidity

The morbidity was calculated as the percentage of kids exhibiting diarrhea (diarrhea scores 1 or 2) relative to the total number of kids present. In the control group, more than 80% of the kids exhibited diarrhea between 7 and 12 days of age, concomitantly with increased oocyst excretion.

Mortality 14 kids died "naturally" and 13 were euthanized on compassionate grounds. The mortality peak, all groups included, was observed at the age of 10-11 days, following the episode of diarrhea.

The cumulative mortality in the group 1 was 91%, in the group 2 was 36%, in the group 3 was 64% and in the group 4 was 55%.

The mortality in the group 1 is significantly higher than in the group 2.

If the kid of the group 4 that did not die from cryptosporidiosis is excluded, the mortality is significantly higher in the control group 1 than in the group 4.

The mortality in the group 3 is reduced.

It should be noted that the average age at the time of death is higher in the treated groups (13.5 for the group 2; 11.7 for the group 3; 16.4 for the group 4) than in the control group (10.7).

Conclusion

The compositions B, C and D according to the invention made it possible to improve the zootechnical performance levels, to reduce diarrhea and to decrease mortality.

The composition C also made it possible to decrease oocyst excretion.

Example 5: Treatment of Cryptosporidiosis Induced in Young Mice (i) Compositions Tested Yeast hulls (Safmannan, France)

(ii) Test of the Effect of the Compounds on *C. parvum* Development

The young mice are inoculated with $5 \times 10^5$ *C. parvum* oocysts.

The oral administration of 500 µg of yeast hulls, hereinafter also called "walls", is carried out the day before the infection with *C. parvum*, and also on the day after and 4 days after the infection, by gavage of C57BL/6 young mice 2 to 3 days old.

The oocysts present in the intestinal content, excreted orally, are counted at 6 days post-inoculation.

Number of young mice:

Experiment 1: n=7-15 young mice

Experiment 2 (n=13 for each batch).

The statistical analysis was carried out by comparing the nontreated batch with each of the batches (nonparametric Mann Whitney test: **$p<0.01$).

Results

At D6 post-infection, the intestinal parasite load makes it possible to evaluate the level of protection obtained compared with the infected but nontreated animals.

The invention claimed is:

1. A method for treating cryptosporidiosis comprising administering to humans or animals infected with *Cryptosporidium* a composition comprising a base agent and an agent for stimulating immunity, wherein the base agent is chosen from chitin or a chitin derivative comprising chitosan, N-acetylglucosamine or glucosamine, and the agent for stimulating immunity is chosen from a yeast cell wall, a yeast extract, selenium, a bacterium of the *Bacillus, Lactobacillus, Bifidobacterium, Enterococcus, Propionibacterium, Pediococcus* or *Lactococcus* genus, a yeast of the *Saccharomyces* or *Kluyveromyces* genus, or a combination thereof.

2. The method as claimed in claim 1, wherein the composition also comprises an antiparasitic agent chosen from an essential oil, active carbon, lauric acid, or combinations thereof.

3. The method as claimed in claim 2, wherein the essential oil is chosen from garlic essential oil, citronella essential oil, cinnamon essential oil, thyme essential oil, oregano essential oil, tea tree essential oil, lemon essential oil, *eucalyptus* essential oil, or combinations thereof.

4. The method as claimed in claim 1, wherein the selenium is in the form of a selenium-enriched yeast, selenium totally or partially extracted from yeast, or combinations thereof.

5. The method as claimed in claim 1, wherein the composition is a food composition, a food supplement or a pharmaceutical composition.

\* \* \* \* \*